US012564680B2

(12) United States Patent
Chang

(10) Patent No.: US 12,564,680 B2
(45) Date of Patent: Mar. 3, 2026

(54) MECHANISM FOR MEDICAMENT DELIVERY DEVICE, AND MEDICAMENT DELIVERY DEVICE COMPRISING MECHANISM

(71) Applicant: SHL MEDICAL AG, Zug (CH)

(72) Inventor: Chun Chang, Stockholm (SE)

(73) Assignee: SHL Medical AG, Zug (CH)

( * ) Notice: Subject to any disclaimer, the term of this patent is extended or adjusted under 35 U.S.C. 154(b) by 659 days.

(21) Appl. No.: 18/015,372

(22) PCT Filed: Jul. 12, 2021

(86) PCT No.: PCT/EP2021/069355
§ 371 (c)(1),
(2) Date: Jan. 10, 2023

(87) PCT Pub. No.: WO2022/023011
PCT Pub. Date: Feb. 3, 2022

(65) Prior Publication Data
US 2023/0277769 A1 Sep. 7, 2023

(30) Foreign Application Priority Data

Jul. 31, 2020 (EP) .................................... 20188960

(51) Int. Cl.
*A61M 5/20* (2006.01)
*A61M 5/315* (2006.01)

(52) U.S. Cl.
CPC ...... *A61M 5/2033* (2013.01); *A61M 5/31501* (2013.01); *A61M 5/31595* (2013.01)

(58) Field of Classification Search
CPC ............ A61M 5/2033; A61M 5/31501; A61M 5/31595
See application file for complete search history.

(56) References Cited

U.S. PATENT DOCUMENTS 6,224,567 B1 5/2001 Roser
8,376,993 B2 2/2013 Cox et al.

FOREIGN PATENT DOCUMENTS

FR 2024089 A5 8/1970

OTHER PUBLICATIONS

International Search Report and Written Opinion for Int. App. No. PCT/EP2021/069355, mailed Sep. 27, 2021.

*Primary Examiner* — Bradley J Osinski
(74) *Attorney, Agent, or Firm* — McDonnell Boehnen Hulbert & Berghoff LLP

(57) ABSTRACT

A mechanism is disclosed having an actuating element, a longitudinal axis, a plunger having at least one first blocking feature and at least one second blocking feature, a plunger force device, a blocking structure rotatable about the longitudinal axis from a first blocking structure position, in which one of the at least one first blocking feature is allowed to pass by the blocking structure and one of the at least one second blocking feature is prevented from passing by the blocking structure, and a second blocking structure position, in which one of the at least one second blocking feature is allowed to pass by the blocking structure, and a transmission configured to transmit a transition of the actuating element between a ready state and a dosing state to a rotation of the blocking structure from the first blocking structure position to the second blocking structure position.

20 Claims, 15 Drawing Sheets

MECHANISM FOR MEDICAMENT DELIVERY DEVICE, AND MEDICAMENT DELIVERY DEVICE COMPRISING MECHANISM

CROSS REFERENCE TO RELATED APPLICATIONS

The present application is a U.S. National Phase Application pursuant to 35 U.S.C. § 371 of International Application No. PCT/EP2021/069355 filed Jul. 12, 2021, which claims priority to European Patent Application No. 20188960.7 filed Jul. 31, 2020. The entire disclosure contents of these applications are herewith incorporated by reference into the present application.

TECHNICAL FIELD

The present disclosure generally relates to a mechanism for a medicament delivery device. In particular, a mechanism for a medicament delivery device and a medicament delivery device comprising such mechanism, are provided.

BACKGROUND

A wide range of medicament delivery devices for self-administration of medicaments are known. Medicament delivery devices, such as pen injectors, auto-injectors and inhalers, typically comprise a housing in which a medicament container containing a medicament is to be arranged. Upon activation of the medicament delivery device, the medicament is expelled through a medicament delivery member, as for example a needle or a nozzle.

In order to deliver medicament from one example of a pen injector, a user may remove a cap to expose a needle and pierce the needle into an injection site. The user may then push a button to cause a plunger to be released proximally. The proximal movement of the plunger pushes a stopper to expel the medicament from a medicament container through the needle.

In order to deliver medicament from one example of an auto-injector, a user may push a needle cover against an injection site. The needle cover thereby moves distally and a needle is exposed and pierces the injection site. The distal movement of the needle cover causes a plunger to be released proximally. The proximal movement of the plunger pushes a stopper to expel the medicament from a medicament container through the needle.

Some of the medicament delivery devices are designed to perform multiple medicament delivery operation and deliver multiple doses. Most of such medicament delivery devices are designed that an end user needs to use he/her manual hand force to push a piston forward and perform the medicament delivery; however, such medicament delivery devices usually require more operation steps and an significant hand force from the end user, e.g. U.S. Pat. No. 8,376,993; or some of such medicament delivery device arranged with a force device configured to push the piston forward; however, those medicament delivery devices usually require the end user to load the force device, e.g. manually twisting an element connected with a spring to accumulate force, before performing the medicament delivery operation. Those medicament delivery devices are therefore more complex for the end user to use.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "rotation", "rotational" and "rotationally" refer to a direction generally perpendicular to the longitudinal direction and at least partially extending around the longitudinal direction.

According to one aspect, there is provided a mechanism for a medicament delivery device, the mechanism comprising an actuating element configured to adopt a ready state and a dosing state; a longitudinal axis; a plunger comprising at least one first blocking feature and at least one second blocking feature, where the at least one first blocking feature and the at least one second blocking feature are axially and circumferentially offset from each other with respect to the longitudinal axis; a plunger force device arranged to force the plunger in a proximal direction along the longitudinal axis; a blocking structure rotatable about the longitudinal axis from a first blocking structure position, in which one of the at least one first blocking feature is allowed to pass by the blocking structure and one of the at least one second blocking feature is prevented from passing by the blocking structure, and a second blocking structure position, in which one of the at least one second blocking feature is allowed to pass by the blocking structure; and a transmission configured to transmit a transition of the actuating element between the ready state and the dosing state to a rotation of the blocking structure from the first blocking structure position to the second blocking structure position.

Since the at least one first blocking feature is allowed to pass by the blocking structure when the blocking structure adopts the first blocking structure position, and the at least one second blocking feature is allowed to pass by the blocking structure when the blocking structure adopts the second blocking structure position, the mechanism can provide multiple doses of medicament delivery. That is, when the blocking structure adopts the first blocking structure position, the plunger force device forces the plunger in the proximal direction to deliver a first dose, and when the blocking structure adopts the second blocking structure position, the plunger force device forces the plunger further in the proximal direction to deliver a second dose. The plunger is thus configured to eject successive doses of medicament from a medicament container without loading action on the force device. The mechanism may be mechanical, i.e. not comprising any electronic components for effecting the multiple dose delivery. When the blocking structure adopts the second blocking structure position, one of the at least one first blocking feature may be prevented from passing by the blocking structure.

Since the at least one first blocking feature and the at least one second blocking feature are axially and circumferentially offset from each other with respect to the longitudinal axis, the at least one first blocking feature and the at least one second blocking feature are staggered.

The actuating element may for example be a cover, such as a needle cover, a push button, or a rotatable button. The plunger force device may be a spring, such as a coil spring or a constant force spring; or a gas canister. The plunger may be cylindrical; the plunger may be a hollow tubular plunger or a plunger rod.

According to one aspect, the blocking structure is a structure that configured to block the proximal movement of the plunger, by engaging with the at least one first blocking feature or at least one second blocking feature. The blocking structure can be a plate shape structure, or a ring shape structure with radially extending rib, or a shelf structure arranged within a housing of the medicament delivery device, or other component that the plunger is movable with.

The blocking structure comprises a through hole. The through hole is designed with a radial width, the radial width is greater enough to allow the plunger with a) only the at least one first blocking features, or b) only the one of the at least one second blocking feature to pass. When the blocking structure is in the first blocking structure position, the through hole is aligned with the at least one first blocking feature such that one of the at least one first blocking feature is allowed to pass through the through hole; and the through hole is misaligned with the at least one second blocking feature, such that the at least one second blocking feature is prevented from passing through the through hole. When the blocking structure is in the second blocking structure position, the through hole is aligned with the at least one second blocking feature such that one of the at least one second blocking feature is allowed to pass through the through hole. The first blocking feature may be misaligned with the through hole, such that the at least one first blocking feature is prevented from passing through the through hole. The through hole can be asymmetric relative to the longitudinal axis.

The at least one first blocking feature may be arranged at a first blocking feature rotational position with respect to the longitudinal axis, and the at least one second blocking feature may be arranged at a second blocking feature rotational position with respect to the longitudinal axis, different from the first blocking feature rotational position. In this way, the at least one first blocking feature and the at least one second blocking feature are circumferentially offset from each other with respect to the longitudinal axis.

The mechanism may be configured to generate a movement of the plunger in the proximal direction when the actuating element transitions from the ready state to the dosing state. Alternatively, the mechanism may be configured to generate a movement of the plunger in the proximal direction when the actuating element transitions from the dosing state to the ready state, such arrangement may be suitable when the actuating element is a push button, so that the medicament will be delivered only when an intentional pressing on the button causes the button reach to the dosing state then back to the ready state; an unintentional pressing on the button, e.g. accidentally touch, will not cause the medicament to be delivered. The transition of the actuating element may be a linear or a rotational transition.

The mechanism may further comprise a housing. In this case, the plunger force device may be arranged between the housing and the plunger. Alternatively, the plunger force device may be arranged between the plunger and a plunger holder of the mechanism. The plunger holder may be movable in relation to the housing.

The transmission may be configured to transmit a transition of the actuating element from the dosing state to the ready state and back to the dosing state, or a transition of the actuating element from the ready state to the dosing state and back to the ready state, to a rotation of the blocking structure from the first blocking structure position to the second blocking structure position. Thus, the mechanism may be configured to generate a proximal movement of the plunger in either the dosing state or in the ready state.

Each of the at least one first blocking feature and the at least one second blocking feature may comprise a protrusion protruding radially outwards with respect to the outer surface of the plunger. Alternatively, each of the at least one first blocking feature and the at least one second blocking feature may comprise a protrusion protruding radially inwards with respect to the outer surface of the plunger. Alternatively, each of the at least one first blocking feature and the at least one second blocking feature may comprise an aperture.

According to one example, each of the at least one first blocking feature and the at least one second blocking feature comprises a pair of two protrusions protruding radially outwards with respect to the outer surface of the plunger. In this case, each protrusion of each pair may be symmetrically arranged with respect to the outer surface of the plunger. That is, the protrusions of each pair may be oppositely arranged on the outer surface of the plunger.

The at least one first blocking feature may be a plurality of first blocking features and the at least one second blocking feature may be a plurality of second blocking features. In this case, the first blocking features and the second blocking features may be alternatingly arranged along the longitudinal axis.

The first blocking features and the second blocking features may be evenly distributed along the longitudinal axis. In this way, the amount of each of the multiple doses of medicament delivery can be equal.

The transmission may comprise a cam profile and a cam follower arranged to follow the cam profile. Thus, when the user forces the actuating element from the ready state to the dosing state, the cam follower will move along the cam profile causing the blocking structure to rotate. The cam profile may be continuous. The cam profile may be a groove, formed by a consecutive cut-out or formed by a consecutive radially protruding ledge, and the cam follower may be a pin guided in the groove. Alternatively, the cam profile may be a protruding rail and the cam follower may be an aperture guided along the rail. As a possible alternative, the transmission may comprise a linkage configured to transmit a transition of the actuating element between the ready state and the dosing state to a rotation of the blocking structure from the first blocking structure position to the second blocking structure position.

The cam profile may comprise a plurality of cam profile sections. In this case, each relative movement between the cam follower and the cam profile through one of the cam profile sections may be transmitted to a rotation of the blocking structure between the first blocking structure position and the second blocking structure position. Each cam profile section may be referred to as a track. The cam profile may thus comprise a plurality of consecutive tracks.

For example, a relative movement between the cam follower and the cam profile through a first cam profile section may be transmitted to a rotation of the blocking structure from the first blocking structure position to the second blocking structure position, and a relative movement between the cam follower and the cam profile through a second cam profile section, following the first cam profile section, may be transmitted to a rotation of the blocking structure from the second blocking structure position to the first blocking structure position. In an example, the cam profile comprises four cam profile sections, a relative movement between the cam follower and the cam profile through a third cam profile section, following the second cam profile section, may be transmitted to a rotation of the blocking structure from the first blocking structure position to the second blocking structure position, and a relative movement between the cam follower and the cam profile through a fourth cam profile section, following the third cam profile section, may be transmitted to a rotation of the blocking structure from the second blocking structure position to the first blocking structure position.

In another example, the transmission may be a gear or a cogwheel.

The mechanism may comprise a rotator. In this example, the rotator may comprise the blocking structure. The rotator may be cylindrical or ring or plate shape.

The cam profile may be provided on the rotator. In this case, the cam profile may be continuous and extend around the circumference of the rotator with respect to the longitudinal axis.

The cam follower may be provided on the actuating element. Alternatively, the cam profile may be provided on the actuating element.

The actuating element may be movable along the longitudinal axis between the ready state and the dosing state. In this case, the actuating element may be rigid. Alternatively, the actuating element may transition between the ready state and the dosing state by deformation of the actuating element. For example, the actuating element may be in a resting state when adopting the ready state and in a compressed state when adopting the dosing state.

In another example, when the actuating element is a rotatable button, the blocking structure may be directly connected with the rotatable button; such as the rotatable button may comprises a user accessible outer portion and a user inaccessible inner portion; the transmission may be the connection between the outer portion and the inner portion; the blocking element is arranged on the inner portion, so that when a user manually rotate the outer portion of the rotatable button from the ready position to the dosing position, the blocking structure is synchronously rotated between the first blocking structure position and the second blocking structure position. In this example, the mechanism may not comprise a rotator as an independent component.

The mechanism may further comprise an actuating element force device arranged to force the actuating element from the dosing state to the ready state. The actuating element force device may be a spring, such as a coil spring; or a resilient arm arranged on the actuating element. In case the mechanism comprises a housing, the actuating element force device may be arranged between the housing and the actuating element.

According to a further aspect, there is provided a medicament delivery device comprising a mechanism according to the present disclosure, and a medicament container. The medicament delivery device may for example be a pen injector, an auto-injector or an inhaler.

The medicament container may comprise a stopper. The plunger may be arranged to push the stopper by movement in the proximal direction to expel medicament contained in the medicament container. The medicament delivery device may further comprise a medicament delivery member, such as a needle or a nozzle; since the medicament delivery device with the mechanism is suitable to deliver multiple doses of the contained medicament, the medicament delivery member can be exchangeable, e.g. safety pen needle.

BRIEF DESCRIPTION OF THE DRAWINGS

Further details, advantages and aspects of the present disclosure will become apparent from the following description taken in conjunction with the drawings, wherein.

DETAILED DESCRIPTION

Figures 1A, 1B, 1C:
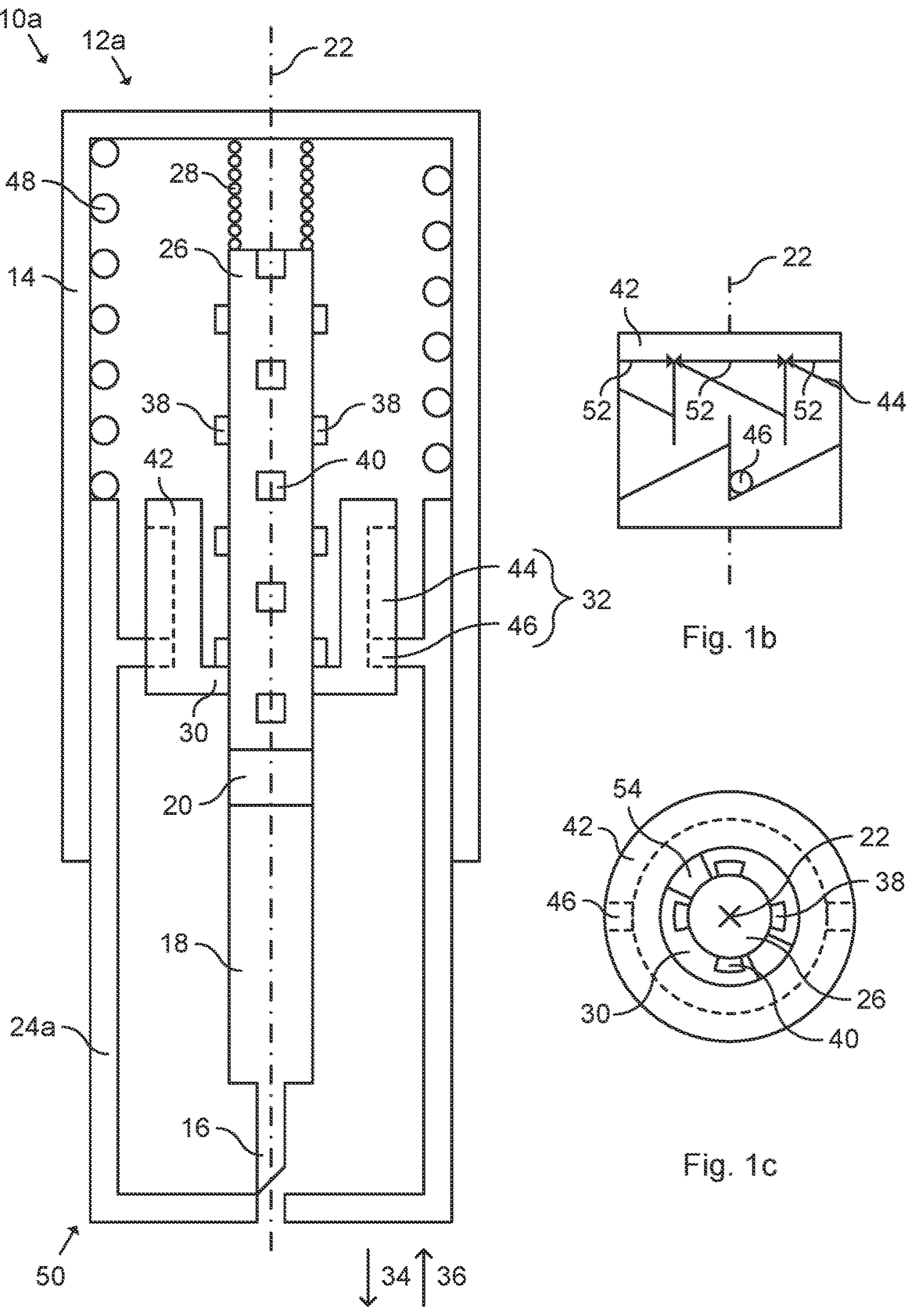
FIG. 1A schematically represents a cross-sectional side view of a medicament delivery device comprising a mechanism with an actuating element in a ready state.
FIG. 1B schematically represents a side view of a rotator and a cam follower of the mechanism in FIG. 1A.
FIG. 1C schematically represents a top view of a plunger, the rotator and the cam follower of the mechanism in FIG. 1A.

In the following, a mechanism for a medicament delivery device and a medicament delivery device comprising such mechanism, will be described. The same or similar reference numerals will be used to denote the same or similar structural features.

FIG. 1A schematically represents a cross-sectional side view of a medicament delivery device 10a. The medicament delivery device 10a of this specific example is an injection device. The medicament delivery device 10a comprises a mechanism 12a, a housing 14, a needle 16 and a medicament container 18 containing medicament. The mechanism 12a is configured to effect multiple dose delivery of medicament from the medicament container 18. The needle 16 is one example of a medicament delivery member according to the present disclosure. The medicament container 18 comprises a stopper 20. The medicament delivery device 10a may comprise a cap for entirely covering the needle.

The mechanism 12a of this example comprises a longitudinal axis 22, a needle cover 24a, a plunger 26, a plunger spring 28, a blocking structure 30 and a transmission 32. FIG. 1A further shows a proximal direction 34 and a distal direction 36, opposite to the proximal direction 34. The cap can be attached to both the housing and the needle cover 24a, so that the cap can also prevent an unintentional movement of the needle cover 24a.

The needle cover 24a is one example of an actuating element according to the present disclosure. The needle cover 24a of this example is cylindrical and concentric with the longitudinal axis 22. Moreover, the needle cover 24a is rigid and rotationally fixed and axially movable relative to the housing 14.

The plunger 26 comprises a plurality of first protrusions 38 and a plurality of second protrusions 40. In this specific example, the plunger 26 comprises four pairs of first protrusions 38 and four pairs of second protrusions 40. Each pair of two first protrusions 38 constitutes one example of a first blocking feature according to the present disclosure. Each pair of two second protrusions 40 (only one second protrusion 40 of each pair of two second protrusions 40 is visible in FIG. 1A) constitutes one example of a second blocking feature according to the present disclosure.

The pairs of first protrusions 38 and the pairs of second protrusions 40 are alternatingly arranged along the longitudinal axis 22. Moreover, the pairs of first protrusions 38 and the pairs of second protrusions 40 are evenly distributed along the longitudinal axis 22. Thus, each distance between each adjacent couple of two pairs of first protrusions 38 and each distance between each adjacent couple of two pairs of second protrusions 40 is equal, and the second protrusions 40 are offset half this distance from the first protrusions 38 along the longitudinal axis 22.

The first protrusions 38 and the second protrusions 40 are thus axially offset from each other with respect to the longitudinal axis 22. That is, each pair of first protrusions 38 and each pair of second protrusions 40 is arranged at a unique position on the plunger 26 along the longitudinal axis 22.

The plunger 26 of this example is cylindrical and concentric with the longitudinal axis 22. Each first protrusion 38 and each second protrusion 40 protrudes radially outwards with respect to the outer surface of the plunger 26. In each pair of first protrusions 38, the two first protrusions 38 are oppositely arranged with respect to the outer surface of the plunger 26. Correspondingly, in each pair of second protrusions 40, the two second protrusions 40 are oppositely arranged with respect to the outer surface of the plunger 26.

Moreover, the first protrusions 38 and the second protrusions 40 are circumferentially offset from each other with respect to the longitudinal axis 22. In the view of the specific example in FIG. 1A, each pair of two first protrusion 38 comprises a left first protrusion 38 and a right first protrusion 38, opposite to the left first protrusion 38, and each pair of two second protrusions 40 comprises a front second protrusion 40 and a rear second protrusion 40 (not visible in FIG. 1A), opposite to the front second protrusion 40.

The plunger spring 28 is one example of a plunger force device according to the present disclosure. In FIG. 1A, the plunger spring 28 is arranged between the housing 14 and the plunger 26. The plunger spring 28 of this example is a coil spring that is concentric with the longitudinal axis 22. In FIG. 1A, the plunger spring 28 is compressed. The plunger spring 28 thereby forces the plunger 26 in the proximal direction 34 along the longitudinal axis 22. Although not illustrated in FIG. 1A, the plunger spring 28 may extend into the plunger 26.

The mechanism 12a of this example further comprises a rotator 42. In FIG. 1A, the blocking structure 30 is arranged in the rotator 42, here at a proximal end thereof. The rotator 42 of this example is cylindrical and concentric with the longitudinal axis 22. The rotator 42 is arranged to rotate about the longitudinal axis 22. In this example, the rotator 42 is prevented from moving axially along the longitudinal axis 22.

The transmission 32 of this example comprises a cam profile 44 and two cam followers 46. Each cam follower 46 is arranged to follow the cam profile 44. Although the transmission 32 of this example comprises two cam followers 46, the transmission 32 may alternatively comprise only one cam follower 46 or more than two cam followers 46. When reference is made to a single cam follower 46, the same applies for any potential further cam follower 46.

In this example, the cam profile 44 is a groove and the cam follower 46 is a pin received in the groove. Preferably, the cam profile 44 is provided on the outer surface of the rotator 42 and the cam follower 46 is provided on the inner surface of the needle cover 24a.

The mechanism 12a of this example further comprises an actuating element spring 48. The actuating element spring 48 is one example of an actuating element force device according to the present disclosure. In FIG. 1A, the actuating element spring 48 is arranged between the housing 14 and the needle cover 24a. The actuating element spring 48 of this example is a coil spring that is concentric with the longitudinal axis 22. In FIG. 1A, the actuating element spring 48 is compressed. The actuating element spring 48 thereby forces the needle cover 24a in the proximal direction 34 along the longitudinal axis 22. This force from the actuating element spring 48 causes the cam follower 46 to be positioned in a proximal region of the cam profile 44.

The blocking structure 30 controls the extension of the plunger 26 in the proximal direction 34. The first protrusions 38 and the second protrusions 40 interact with the blocking structure 30. In FIG. 1A, one pair of first protrusions 38 is engaged with the blocking structure 30, so that the pair of first protrusion 38 is blocked by the blocking structure 30. Although the plunger 26 is forced in the proximal direction 34 by the plunger spring 28, the engagement between the pair of first protrusions 38 and the blocking structure 30 prevents the plunger 26 from moving in the proximal direction 34.

In FIG. 1A, the needle cover 24a is in a ready state 50. In the ready state 50, the needle cover 24a covers the needle 16. The needle cover 24a is movable from the ready state 50 to a dosing state by movement in the distal direction 36 along the longitudinal axis 22. The needle cover 24a is thereby configured to adopt the ready state 50 and the dosing state.

FIG. 1B schematically represents a side view of the rotator 42 and the cam follower 46 in FIG. 1A. The cam profile 44 extends continuously around the circumference of the rotator 42. As shown in FIG. 1B, the cam profile 44 comprises a plurality of consecutive cam profile sections 52. In this example, the cam profile 44 comprises four cam profile sections 52. Each cam profile section 52 has the same design.

FIG. 1C schematically represents a top view of the plunger 26, the rotator 42 and the cam follower 46 in FIG. 1A. As shown in FIG. 1C, the blocking structure 30 comprises a through hole 54. In one example, as shown in FIG. 1C, in the initial (before used) rotational position of the blocking structure 30, none of the first protrusions 38 and the second protrusions 40 is aligned with the through hole 54. The blocking structure 30 thereby blocks the plunger 26 from moving in the proximal direction 34.

Figure 2:
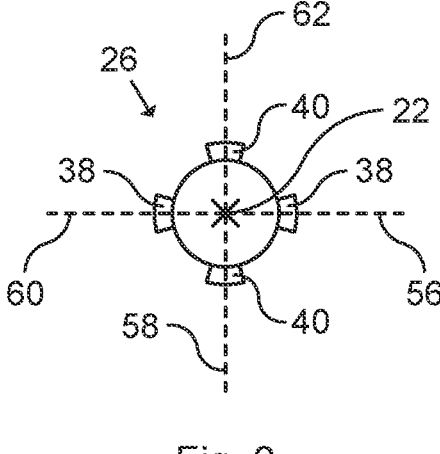
FIG. 2 schematically represents a top view of the plunger.

FIG. 2 schematically represents a top view of the plunger 26 of one example. As can be gathered from FIG. 2, half of the first protrusions 38 are positioned at a first blocking feature rotational position 56 with respect to the longitudinal axis 22, and half of the second protrusions 40 are positioned at a second blocking feature rotational position 58, angularly spaced 90 degrees from the first blocking feature rotational position 56 with respect to the longitudinal axis 22. The other half of the first protrusions 38 are positioned at a third blocking feature rotational position 60, angularly spaced 90 degrees from the second blocking feature rotational position 58 with respect to the longitudinal axis 22. The other half of the second protrusions 40 are positioned at a fourth blocking feature rotational position 62, angularly spaced 90 degrees from the third blocking feature rotational position 60 with respect to the longitudinal axis 22. The first protrusions 38 and the second protrusions 40 are thus circumferentially offset from each other with respect to the longitudinal axis 22.

It should be noted that, the angular offset degrees between one of the first protrusions and one of the second protrusions is dependent on the rotational angle of the rotator. Except the first rotation of the rotator (the rotation occurred with the first time of use of a new medicament delivery device), the rotator will be rotated when a) the cam follower moves along one cam profile section and b) the cam follower slides from one cam profile section to another adjacent cam profile section. The sum of the rotational angle of these two rotations of the rotator should be enough to release the plunger, so that the angular offset degrees between one of the first protrusions and one of the second protrusions is dependent on such sum of the rotational angle.

Figure 3:
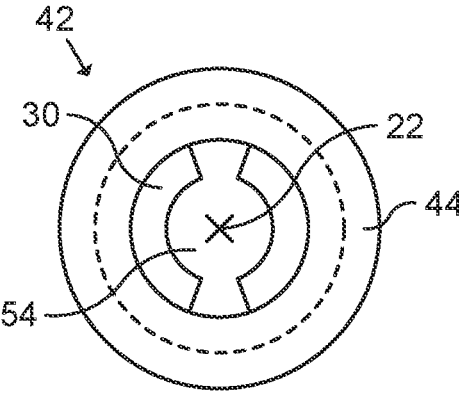
FIG. 3 schematically represents a top view of the rotator.

FIG. 3 schematically represents a top view of the rotator 42. In FIG. 3, the blocking structure 30 and the through hole 54 thereof can be seen more clearly. The through hole 54 is asymmetric with respect to the longitudinal axis 22.

Figures 4A, 4B, 4C:
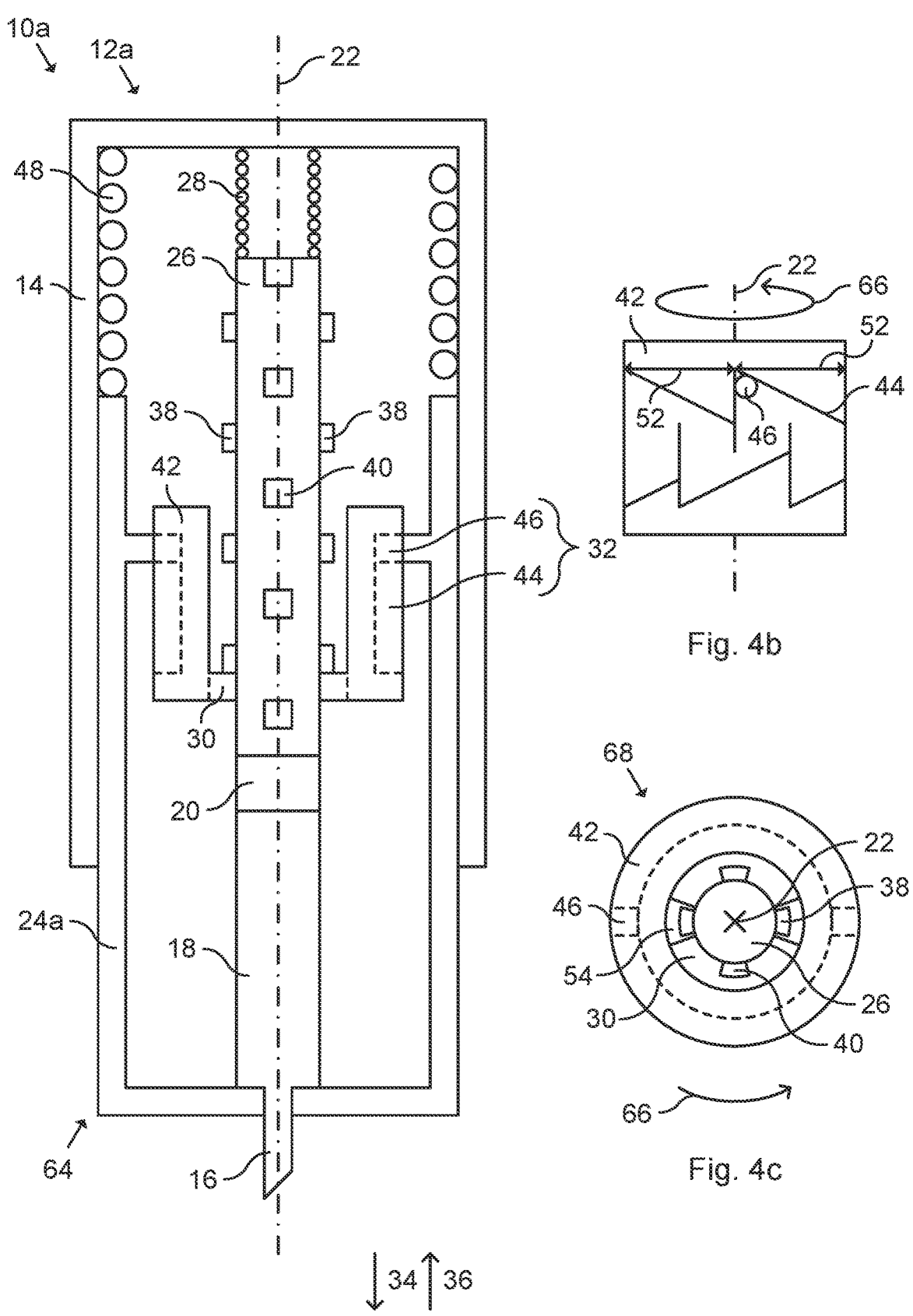
FIG. 4A schematically represents a cross-sectional side view of the medicament delivery device when actuating element adopts a dosing state.
FIG. 4B schematically represents a side view of the rotator and the cam follower in FIG. 4A.
FIG. 4C schematically represents a top view of the plunger, the rotator and the cam follower in FIG. 4A when a blocking structure of the rotator adopts a first blocking structure position.

FIG. 4A schematically represents a cross-sectional side view of the medicament delivery device 10a. In FIG. 4A, the needle cover 24a has moved linearly in the distal direction 36 from the ready state 50 to the dosing state 64. The movement causes the actuating element spring 48 to be compressed. A user may grab the medicament delivery device 10a and push the needle cover 24a against an injection site (not shown) to cause the movement of the needle cover 24a in the distal direction 36 and to cause the needle 16 to pierce the injection site.

The needle cover 24a moves in the distal direction 36, so that the cam follower 46 moves synchronously in the distal direction 36. The needle cover 24a is rotationally fixed relative to the housing 14 and the rotator is rotatable relative to the longitudinal axis 22, therefore, the movement of the cam follower 46 in the distal direction 36 causes the cam follower 46 to drive the rotator 42 to rotate by the engagement of the cam profile 44 with the cam follower 46, as shown with arrow 66 in FIG. 4B.

As shown in FIG. 4C, the blocking structure 30 now rotates, together with the rotator, from the initial (before used) rotational position to a first blocking structure position 68. In the first blocking structure position 68, the through hole 54 is aligned with the first protrusions 38. The blocking structure 30 thereby no longer blocks movement of the plunger 26 in the proximal direction 34 by engagement between the blocking structure 30 and the first protrusions 38. The plunger spring 28 thereby forces the plunger 26 to move in the proximal direction 34.

It should be noted that, alternatively, in the initial (before used) rotational position of the blocking structure, the first protrusions are misaligned with the through hole 54, but the second protrusions are aligned with the through hole 54; since the most proximal second protrusions in this example is arranged proximally relative to the most proximal first protrusions, so the engagement between the most proximal second protrusions and the blocking structure prevents the plunger from moving in the proximal direction, even the first protrusions are allowed to pass by the blocking structure by aligning with the through hole. In this case, the initial (before used) rotational position of the blocking structure is same as the first blocking structure position.

Figures 5A, 5B, 5C:
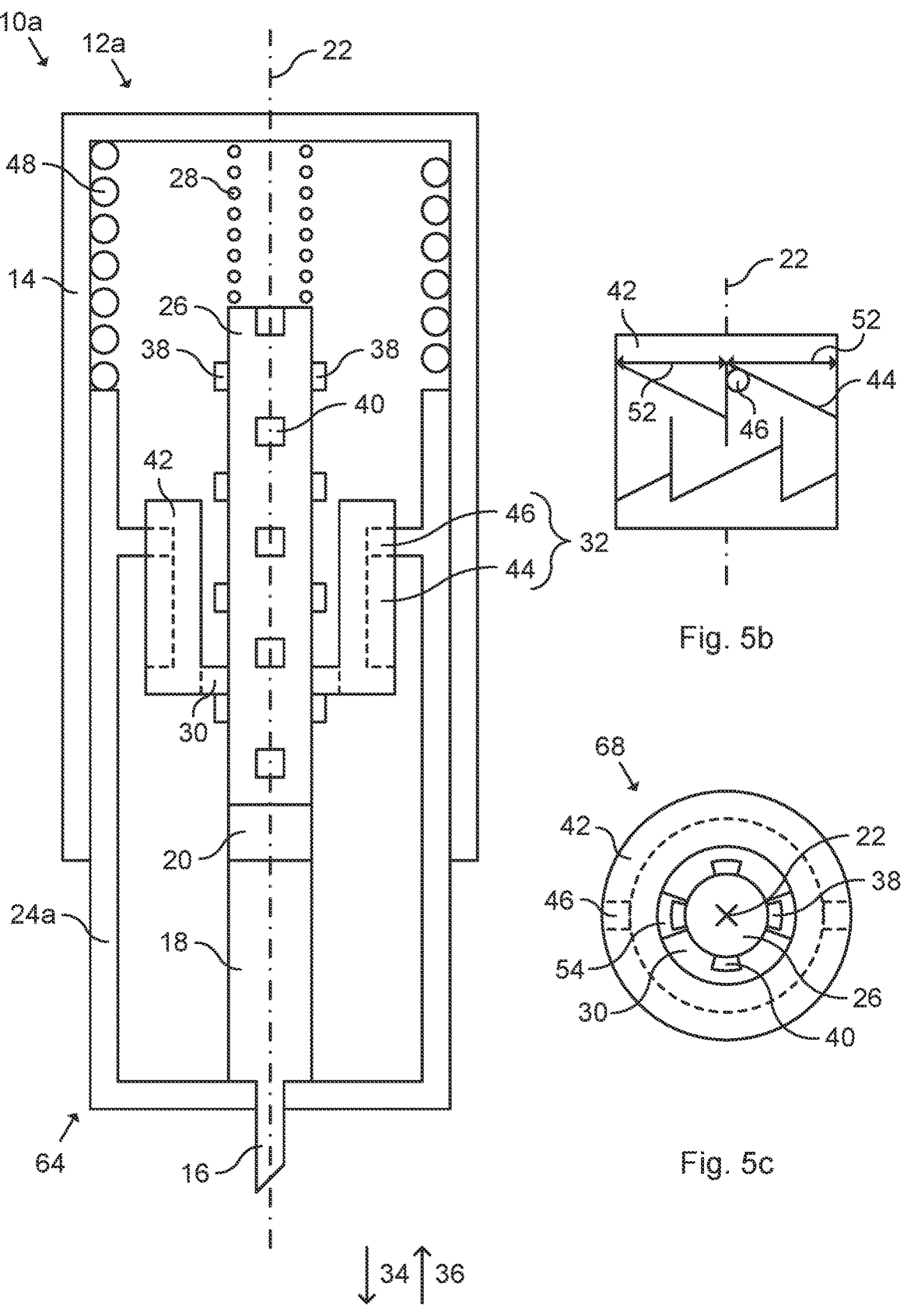
FIG. 5A schematically represents a cross-sectional side view of the medicament delivery device when the plunger has moved in a proximal direction.
FIG. 5B schematically represents a side view of the rotator and the cam follower in FIG. 5A.
FIG. 5C schematically represents a top view of the plunger, the rotator and the cam follower in FIG. 5A.

FIG. 5A schematically represents a cross-sectional side view of the medicament delivery device 10a when the plunger 26 has moved in a proximal direction 34, FIG. 5B schematically represents a side view of the rotator 42 and the cam follower 46 in FIG. 5A, and FIG. 5C schematically represents a top view of the plunger 26, the rotator 42 and the cam follower 46 in FIG. 5A. In FIGS. 5A-5C, one pair of first protrusions 38 has moved through the through hole 54 of the blocking structure 30. The movement of the plunger 26 in the proximal direction 34 causes the plunger 26 to push the stopper 20 to expel a first dose of medicament from the medicament container 18 into the injection site. As shown in FIGS. 5A and 5C, the blocking structure 30 stops the plunger 26 when the next pair of second protrusions 40 comes in contact with the blocking structure 30. The mechanism 12a of this example is thus configured to generate a movement of the plunger 26 in the proximal direction 34 when the needle cover 24a moves from the ready state 50 to the dosing state 64.

Figures 6A, 6B, 6C:
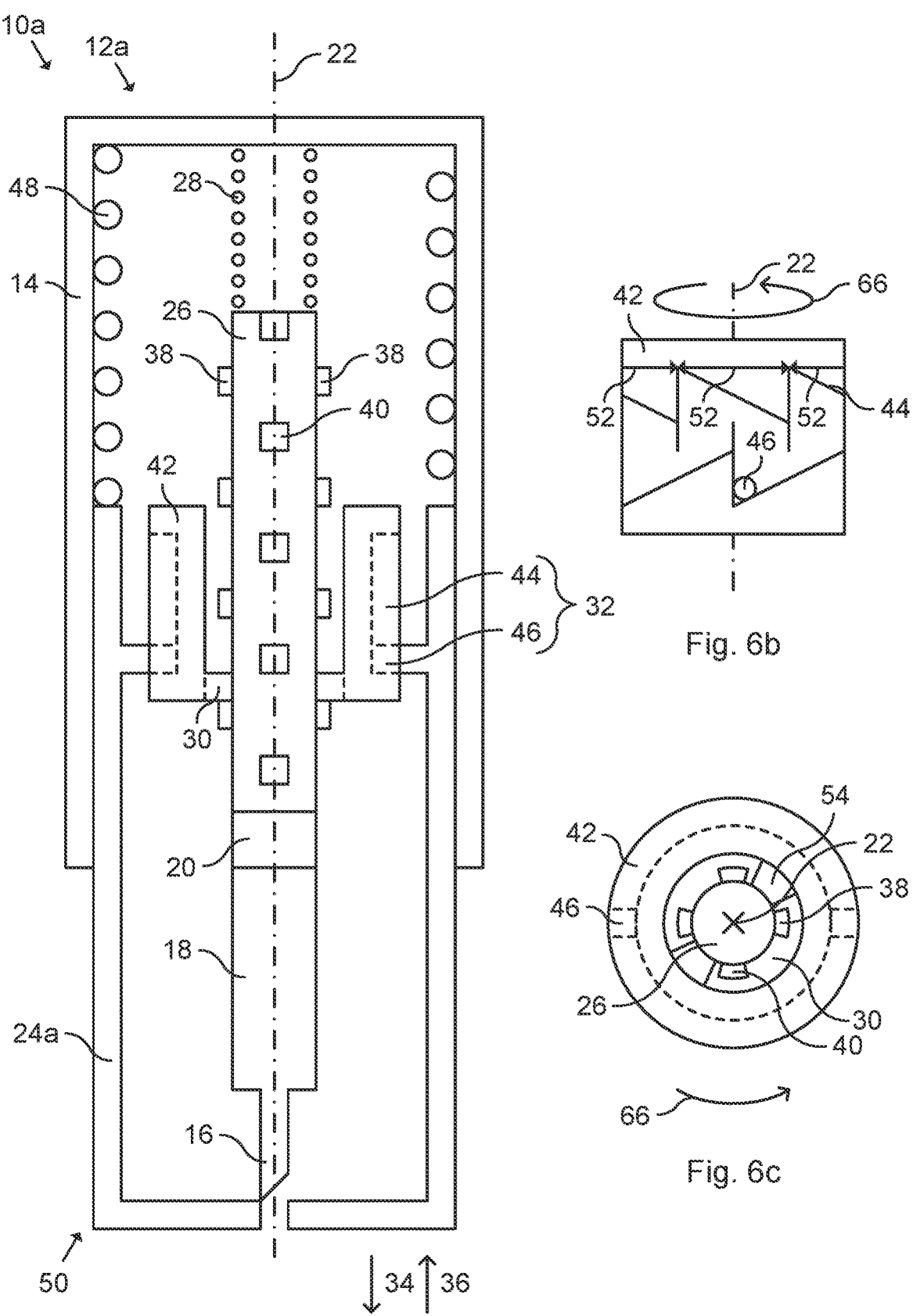
FIG. 6A schematically represents a cross-sectional side view of the medicament delivery device when the actuating element has returned to the ready state.
FIG. 6B schematically represents a side view of the rotator and the cam follower in FIG. 6A.
FIG. 6C schematically represents a top view of the plunger, the rotator and the cam follower in FIG. 6A.

FIG. 6A schematically represents a cross-sectional side view of the medicament delivery device 10a when the needle cover 24a has returned to the ready state 50, FIG. 6B schematically represents a side view of the rotator 42 and the cam follower 46 in FIG. 6A, and FIG. 6C schematically represents a top view of the plunger 26, the rotator 42 and the cam follower 46 in FIG. 6A. When the user removes the medicament delivery device 10a from the injection site, the actuating element spring 48 forces the needle cover 24a to move linearly in the proximal direction 34 from the dosing state 64 back to the ready state 50. Since the needle cover 24a moves in the proximal direction 34, also the cam follower 46 moves in the proximal direction 34. The movement of the cam follower 46 in the proximal direction 34 causes the cam follower 46 to drive the rotator 42 to rotate further by the engagement of the cam profile 44 with the cam follower 46, as shown in FIG. 6B.

Figures 7A, 7B, 7C:
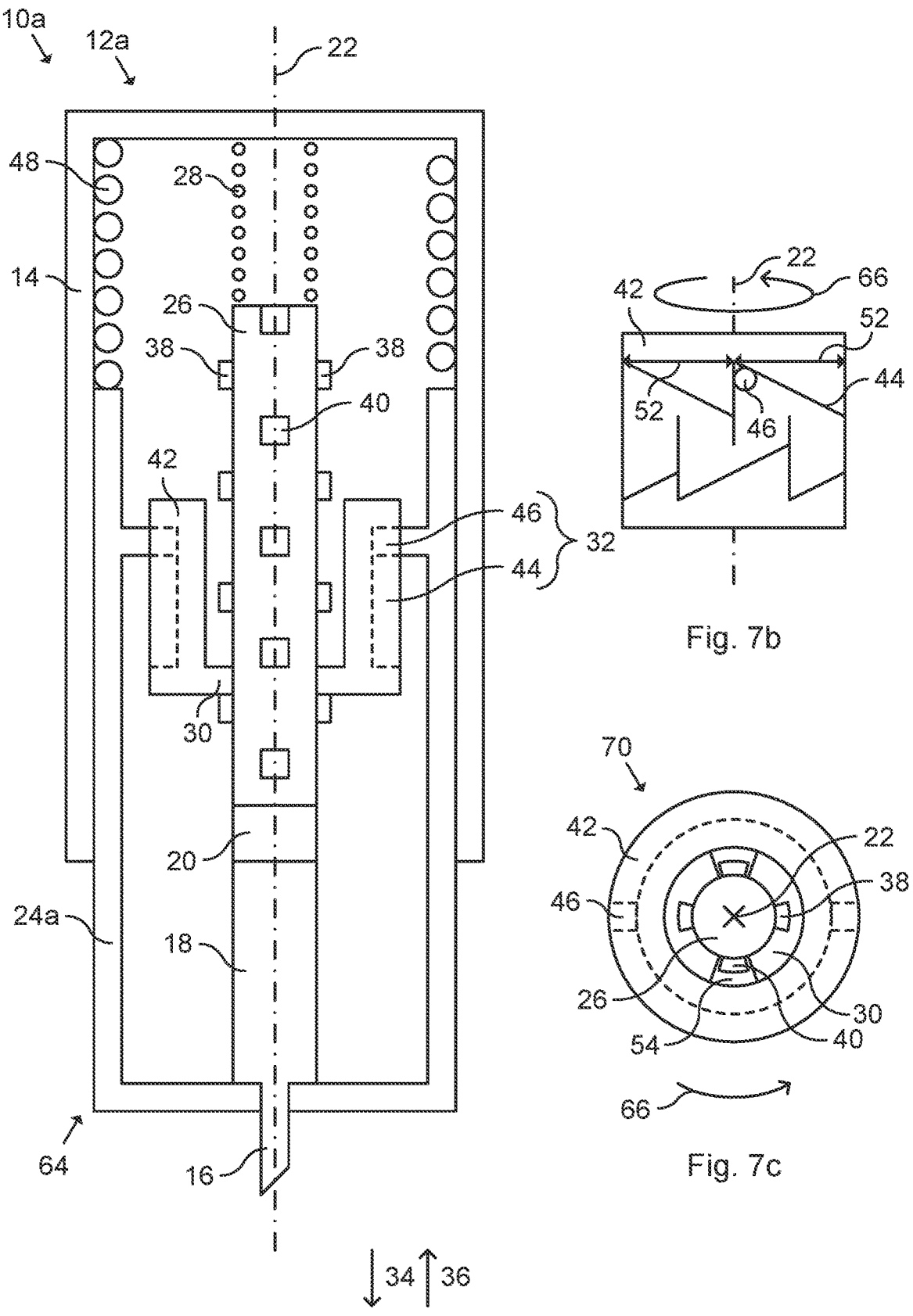
FIG. 7A schematically represents a cross-sectional side view of the medicament delivery device when the actuating element again adopts the dosing state.
FIG. 7B schematically represents a side view of the rotator and the cam follower in FIG. 7A.
FIG. 7C schematically represents a top view of the plunger, the rotator and the cam follower in FIG. 7A when the blocking structure of the rotator adopts a second blocking structure position.

FIG. 7A schematically represents a cross-sectional side view of the medicament delivery device 10a when the needle cover 24a again adopts the dosing state 64, FIG. 7B schematically represents a side view of the rotator 42 and the cam follower 46 in FIG. 7A, and FIG. 7C schematically represents a top view of the plunger 26, the rotator 42 and the cam follower 46 in FIG. 7A. In FIG. 7A, the needle cover 24a has again moved in the distal direction 36 from the ready state 50 to the dosing state 64. The movement again causes the actuating element spring 48 to be compressed. A user may grab the medicament delivery device 10a a second time for a second medicament delivery and push the needle cover 24a against an injection site (not shown) to cause movement of the needle cover 24a in the distal direction 36 and to cause the needle 16 to pierce the injection site.

Since the needle cover 24a moves in the distal direction 36, also the cam follower 46 moves in the distal direction 36. The movement of the cam follower 46 in the distal direction 36 causes the cam follower 46 to drive the rotator 42 to rotate further by the engagement of the cam profile 44 with the cam follower 46, as shown in FIG. 7B.

As shown in FIG. 7C, the blocking structure 30 now adopts a second blocking structure position 70. In the second blocking structure position 70, the through hole 54 is aligned with the second protrusions 40. The blocking structure 30 thereby no longer blocks movement of the plunger 26 in the proximal direction 34 by engagement between the blocking structure 30 and the second protrusions 40. The plunger spring 28 thereby forces the plunger 26 to move in the proximal direction 34.

Figures 8A, 8B, 8C:
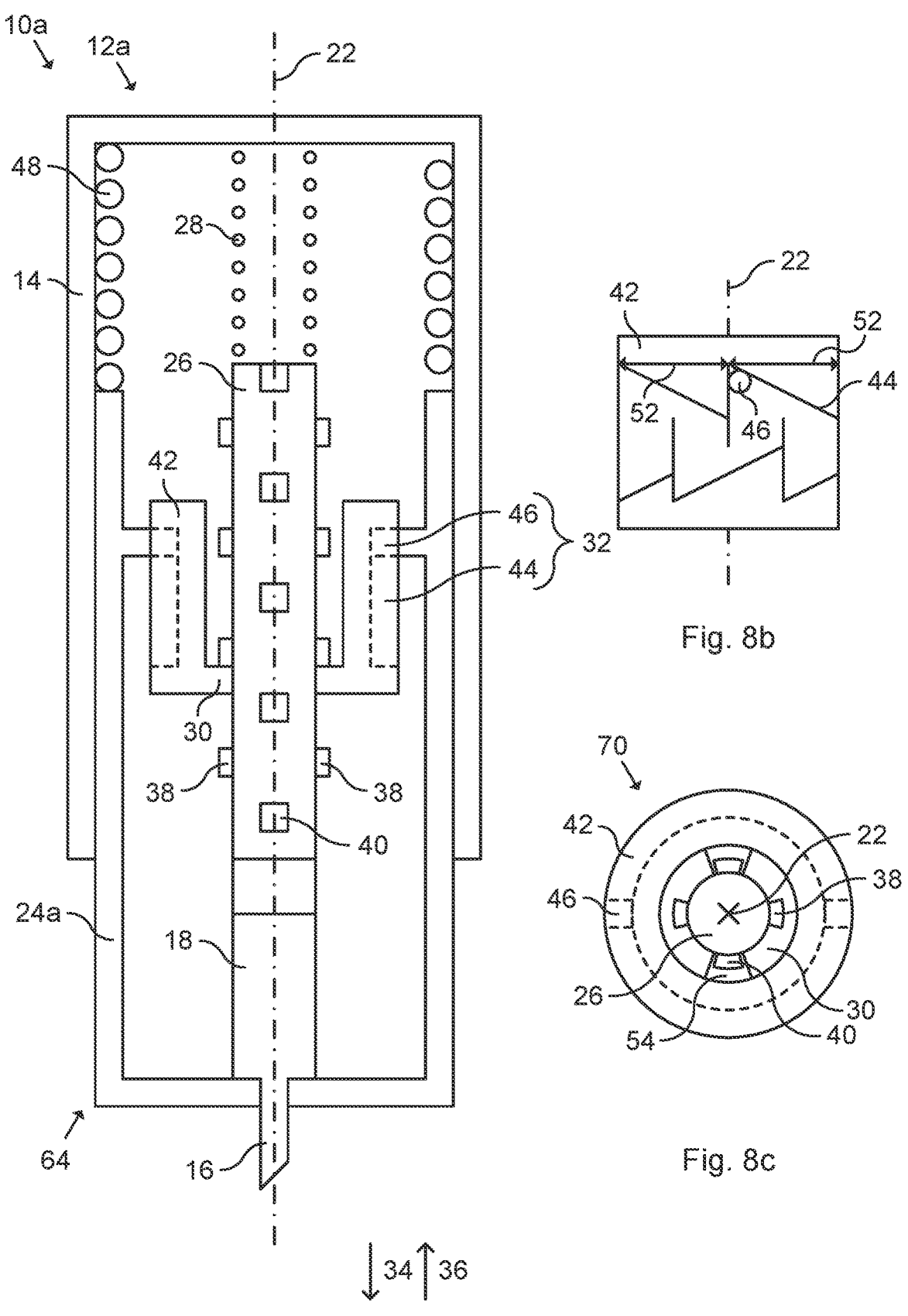
FIG. 8A schematically represents a cross-sectional side view of the medicament delivery device when the plunger has moved further in the proximal direction.
FIG. 8B schematically represents a side view of the rotator and the cam follower in FIG. 8A.
FIG. 8C schematically represents a top view of the plunger, the rotator and the cam follower in FIG. 8A.

FIG. 8A schematically represents a cross-sectional side view of the medicament delivery device 10a when the plunger 26 has moved further in the proximal direction 34, FIG. 8B schematically represents a side view of the rotator 42 and the cam follower 46 in FIG. 8A, and FIG. 8C schematically represents a top view of the plunger 26, the rotator 42 and the cam follower 46 in FIG. 8A. In FIGS. 8A-8C, one pair of second protrusions 40 has moved through the through hole 54 of the blocking structure 30. The movement of the plunger 26 in the proximal direction 34 causes the plunger 26 to push the stopper 20 further in the proximal direction 34 to expel a second dose of medicament from the medicament container 18 into the injection site. As shown in FIGS. 8A and 8C, the blocking structure 30 stops the plunger 26 when the next pair of first protrusions 38 comes in contact with the blocking structure 30.

The transmission 32 is thus arranged to transmit a transition of the needle cover 24a from the dosing state 64 in FIGS. 4A-5C, to the ready state 50 in FIGS. 6A-6C, and back to the dosing state 64 in FIGS. 7A-7C, to a rotation of the blocking structure 30 from the first blocking structure position 68 to the second blocking structure position 70. The next time the needle cover 24a is moved from the dosing state 64, to the ready state 50, and back to the dosing state 64, the blocking structure 30 rotates from the second blocking structure position 70 to the first blocking structure position 68.

Moreover, the blocking structure 30 is thus rotatable about the longitudinal axis 22 from the first blocking structure position 68 in FIGS. 4A-5C, in which one pair of the first protrusions 38 is allowed to pass by the blocking structure 30 and one pair of the second protrusions 40 is blocked by the blocking structure 30, to the second blocking structure position 70 in FIGS. 7A-8C, in which one pair of the second protrusions 40 is allowed to pass by the blocking structure 30 and one pair of the first protrusions 38 is blocked by the blocking structure 30.

Furthermore, a movement of the cam follower 46 from the position on the cam profile 44 according to FIG. 5B, through one cam profile section 52, and to the position on the cam profile 44 according to FIG. 8B, corresponds to a rotation of the blocking structure 30 from the first blocking structure position 68 in FIG. 5C to the second blocking structure position 70 in FIG. 8C. Thus, each relative movement between the cam follower 46 and the cam profile 44 through one of the cam profile sections 52 is transmitted to a rotation of the blocking structure between the first blocking structure position 68 and the second blocking structure position 70.

Figures 9A, 9B, 9C:
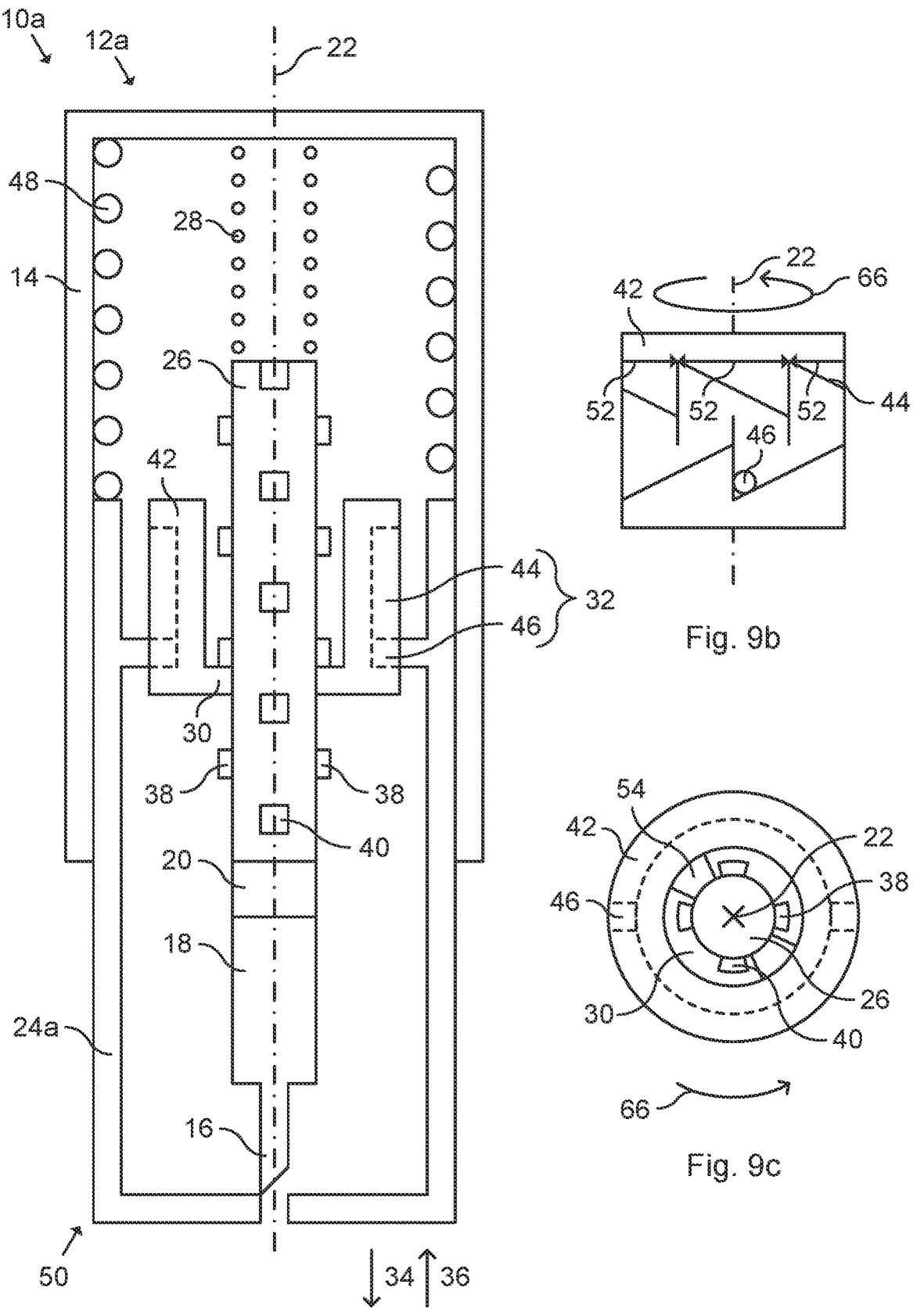
FIG. 9A schematically represents a cross-sectional side view of the medicament delivery device when the actuating element has again returned to the ready state.
FIG. 9B schematically represents a side view of the rotator and the cam follower in FIG. 9A.
FIG. 9C schematically represents a top view of the plunger, the rotator and the cam follower in FIG. 9A.

FIG. 9A schematically represents a cross-sectional side view of the medicament delivery device 10a when the needle cover 24a has again returned to the ready state 50, FIG. 9B schematically represents a side view of the rotator 42 and the cam follower 46 in FIG. 9A, and FIG. 9C schematically represents a top view of the plunger 26, the rotator 42 and the cam follower 46 in FIG. 9A. When the user removes the medicament delivery device 10a from the injection site, the actuating element spring 48 again forces the needle cover 24a to move in the proximal direction 34 from the dosing state 64 back to the ready state 50. Since the needle cover 24a moves in the proximal direction 34, also the cam follower 46 moves in the proximal direction 34. The movement of the cam follower 46 in the proximal direction 34 causes the cam follower 46 to drive the rotator 42 to rotate further by the engagement of the cam profile 44 with the cam follower 46, as shown in FIG. 9B. In the same way as described above, the user can perform a plurality of further deliveries of medicament or "shots" by means of the medicament delivery device 10*a*. As shown in FIG. 9A, there are three pairs of first protrusions 38 and three pairs of second protrusions 40 available distally of the blocking structure 30. Thus, six additional medicament deliveries can be performed in this specific example.

Figures 10A, 10B, 10C:
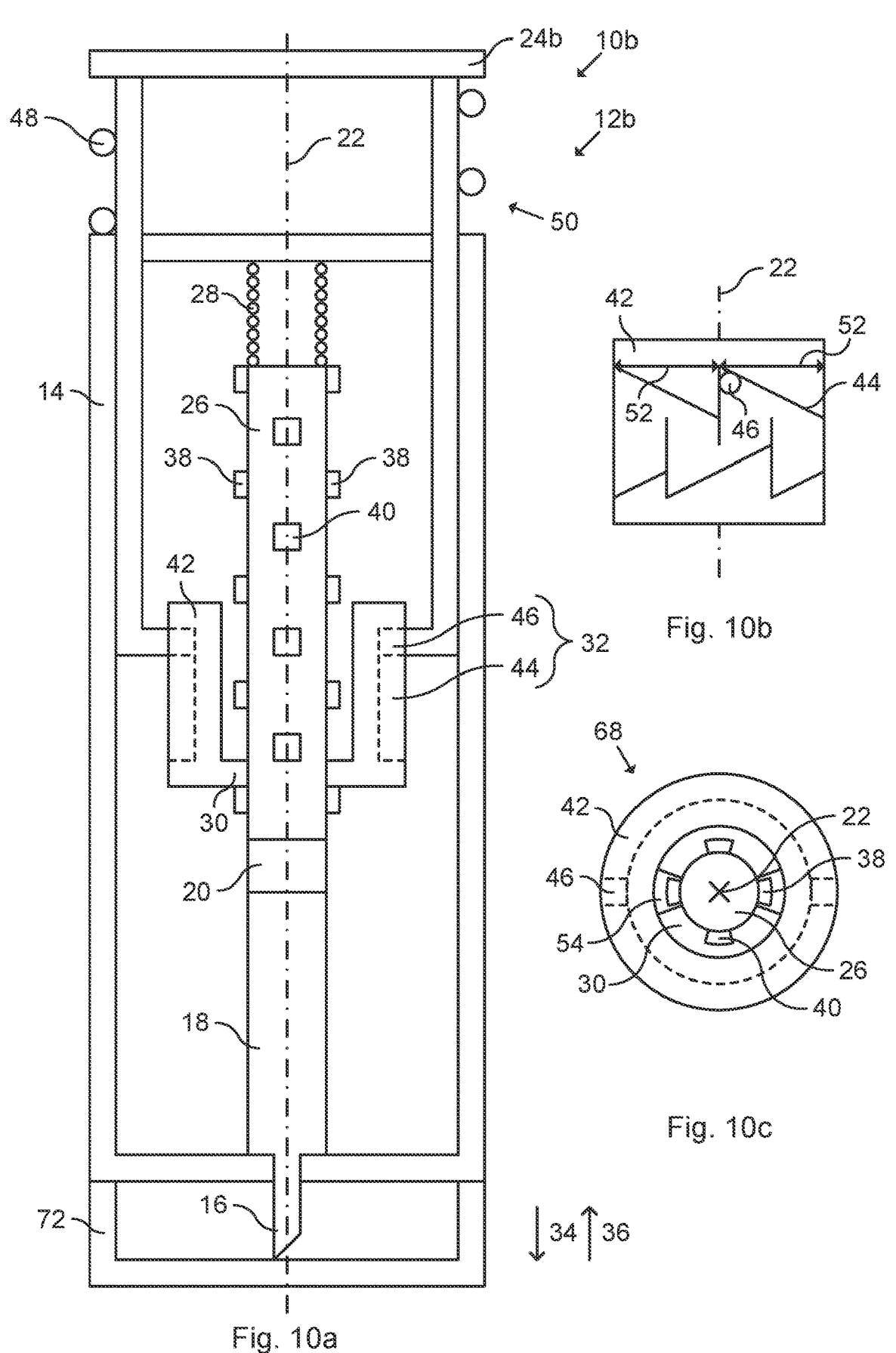
FIG. 10A schematically represents a cross-sectional side view of a further example of a medicament delivery device comprising a further example of a mechanism with a further example of an actuating element in a ready state.
FIG. 10B schematically represents a side view of a rotator and a cam follower of the mechanism in FIG. 10A.
FIG. 10C schematically represents a top view of a plunger, the rotator and the cam follower of the mechanism in FIG. 10A when a blocking structure of the rotator adopts a first blocking structure position.

FIG. 10A schematically represents a cross-sectional side view of a further example of a medicament delivery device 10*b*. Mainly differences with respect to FIGS. 1A-9C will be described. The medicament delivery device 10*b* of the example in FIG. 10A is an injector and comprises a mechanism 12*b*. The mechanism 12*b* comprises a button 24*b*. Instead of the needle cover 24*a*, the button 24*b* is a further example of an actuating element according to the present disclosure.

The medicament delivery device 10*b* further comprises a cap 72. The cap 72 is connected to the housing 14. The cap 72 thereby covers the needle 16. It should be noted that, the medicament delivery device may also comprise a needle cover, as mentioned above, for surrounding the needle when the cap is removed from the medicament delivery device; as mentioned above, the cap can be arranged to both attached to the needle cover and the housing, so that any unintentional movement of the needle cover relative to the housing can be prevented before or after used, and the risk of an injury by the needle can therefore be prevented.

The button 24*b* of this example is provided on a distal end of the medicament delivery device 10*b*. The button 24*b* is concentric with the longitudinal axis 22. Moreover, the button 24*b* is rigid and axially movable and rotationally fixed relative to the housing 14. In this embodiment, the rotator 42 may be axially fixed to the housing 14, and rotational relative to the longitudinal axis 22 as mentioned above.

The actuating element spring 48 is compressed between the button 24*b* and the housing 14. The actuating element spring 48 thereby forces the button 24*b* in the distal direction 36 along the longitudinal axis 22. This force from the actuating element spring 48 causes the cam follower 46 to be positioned in a distal region of the cam profile 44 (arranged on the rotator 42), since the cam follower 46 is arranged on the button 24*b*. In FIG. 10A, one pair of second protrusions 40 is engaged with the blocking structure 30, so that the pair of second protrusions 40 is blocked by the blocking structure 30. The engagement between the pair of second protrusions 40 and the blocking structure 30 prevents the plunger 26 from moving in the proximal direction 34.

In FIG. 10A, the button 24*b* is in the ready state 50. The button 24*b* is movable from the ready state 50 to the dosing state 64 by movement in the proximal direction 34 along the longitudinal axis 22. The button 24*b* is thereby configured to adopt the ready state 50 and the dosing state 64.

FIG. 10B schematically represents a side view of the rotator 42 and the cam follower 46 of the mechanism 12*b* in FIG. 10A, and FIG. 10C schematically represents a top view of the plunger 26, the rotator 42 and the cam follower 46 of the mechanism 12*b* in FIG. 10A. As shown in FIG. 10C, the blocking structure 30 of the rotator 42 adopts the first blocking structure position 68. A user may remove the cap 72 to expose or attach the needle 16, grab the medicament delivery device 10*b* and pierce an injection site by the needle 16.

Figures 11A, 11B, 11C:
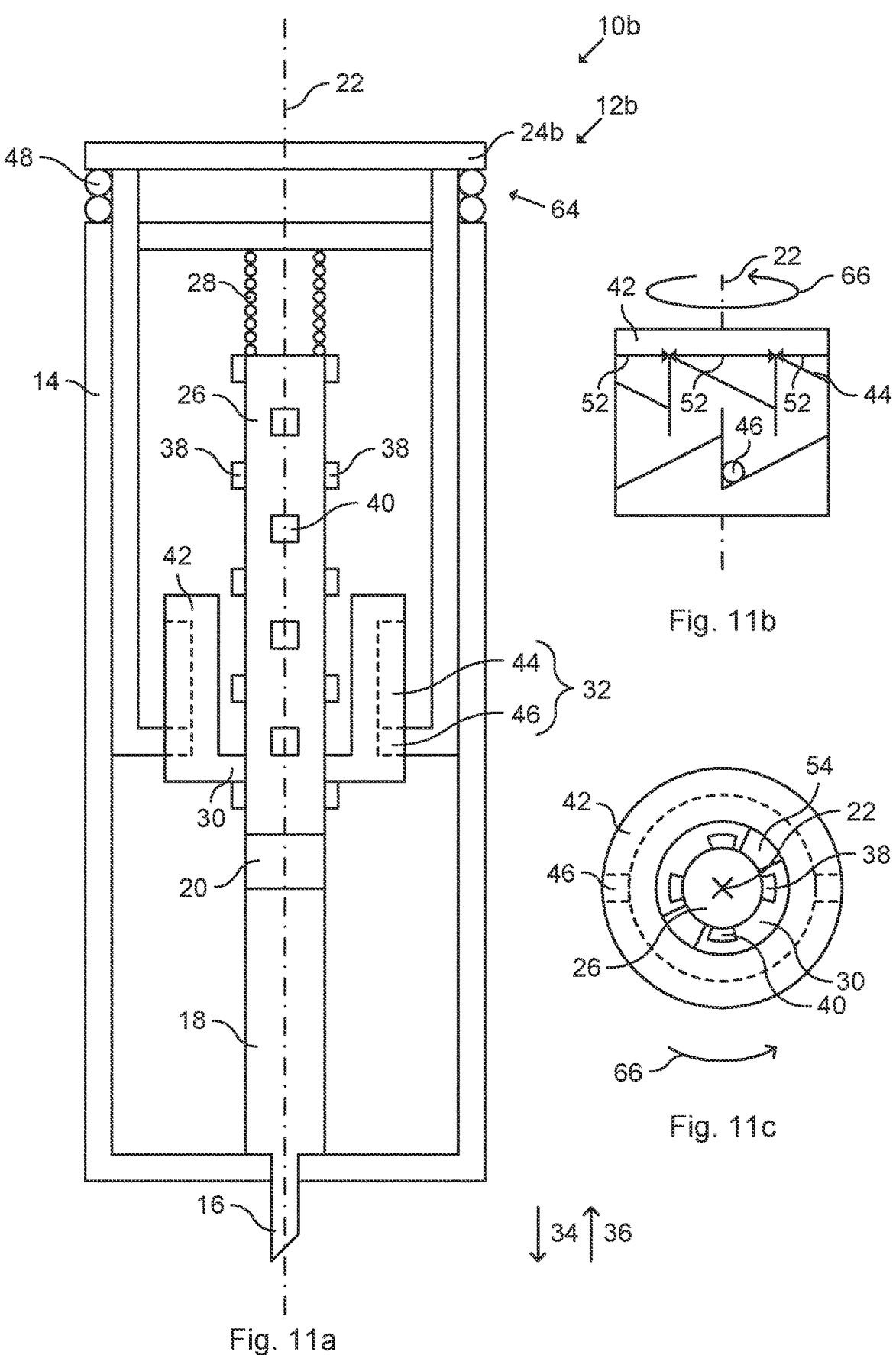
FIG. 11A schematically represents a cross-sectional side view of the medicament delivery device in FIGS. 10A-10C when the actuating element adopts a dosing state.
FIG. 11B schematically represents a side view of the rotator and the cam follower in FIG. 11A.
FIG. 11C schematically represents a top view of the plunger, the rotator and the cam follower in FIG. 11A.

FIG. 11A schematically represents a cross-sectional side view of the medicament delivery device 10B in FIGS. 10A-10C when the button 24*b* is pressed to adopt the dosing state 64, FIG. 11B schematically represents a side view of the rotator 42 and the cam follower 46 in FIG. 11A, and FIG. 11C schematically represents a top view of the plunger 26, the rotator 42 and the cam follower 46 in FIG. 11A. When the user pushes the button 24*b*, the button 24*b* moves linearly in the proximal direction 34. Thereby, also the cam follower 46 moves in the proximal direction 34. The movement of the button 24*b* in the proximal direction 34 causes the actuating element spring 48 to be compressed. Since the button 24*b* is rotationally fixed to the housing, the movement of the cam follower 46 in the proximal direction 34 causes the cam follower 46 to drive the rotator 42 to rotate by the engagement of the cam profile 44 with the cam follower 46, as shown with arrow 66 in FIG. 11B. The blocking structure 30 thereby rotates away from the first blocking structure position 68.

In the initial (before used) rotational position of the blocking structure 30 in FIG. 11C, none of the first protrusions 38 and the second protrusions 40 is aligned with the through hole 54; or alternatively, only the most proximal pair of first protrusions 38 is misaligned with the through hole. The blocking structure 30 thereby blocks the plunger 26 from moving in the proximal direction 34.

Figures 12A, 12B, 12C:
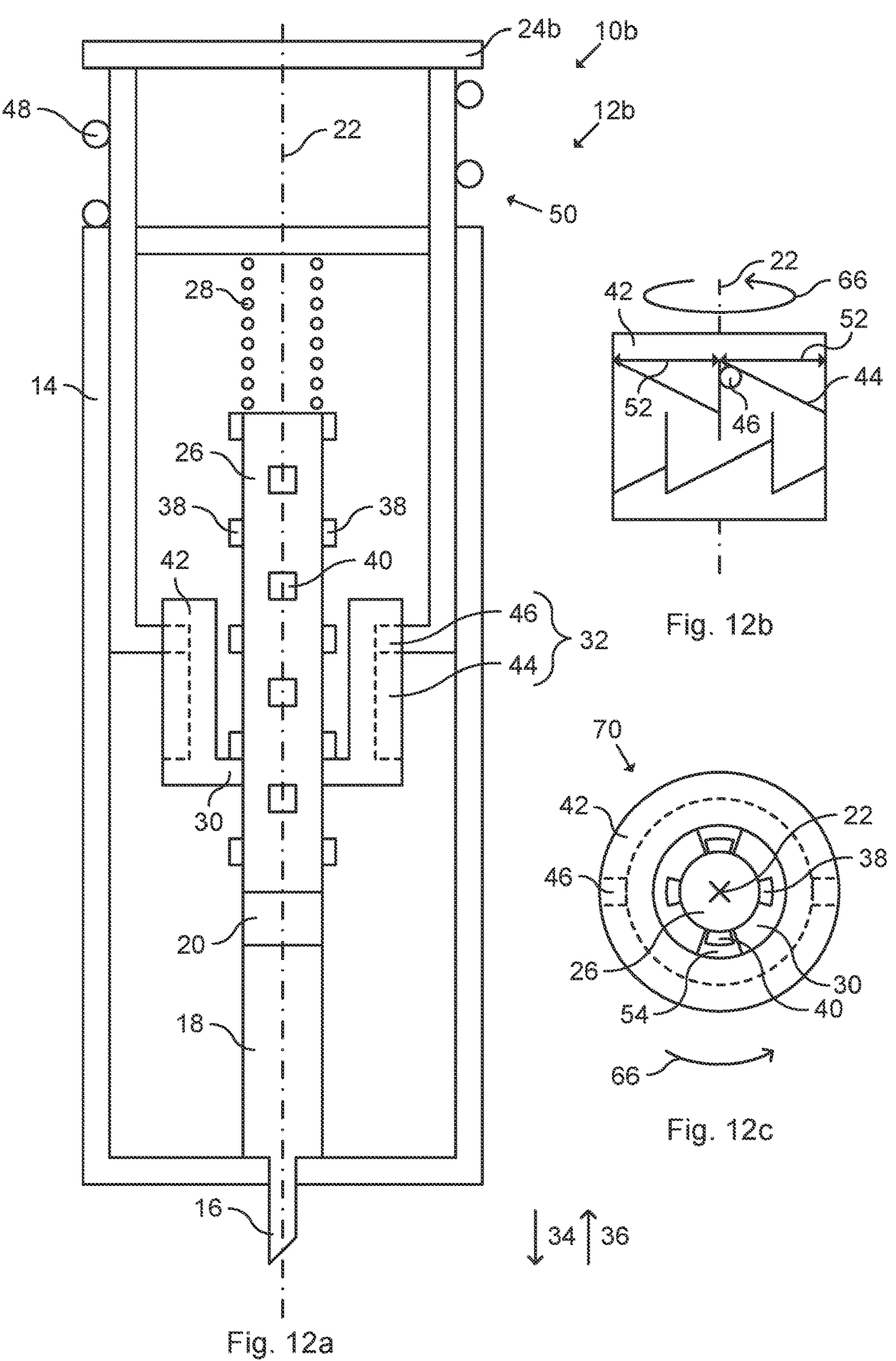
FIG. 12A schematically represents a cross-sectional side view of the medicament delivery device when the plunger has moved in the proximal direction and the actuating element has returned to the ready state.
FIG. 12B schematically represents a side view of the rotator and the cam follower in FIG. 12A.
FIG. 12C schematically represents a top view of the plunger, the rotator and the cam follower in FIG. 12A.

FIG. 12A schematically represents a cross-sectional side view of the medicament delivery device 10*b* when the plunger 26 has moved in the proximal direction 34, FIG. 12B schematically represents a side view of the rotator 42 and the cam follower 46 in FIG. 12A, and FIG. 12C schematically represents a top view of the plunger 26, the rotator 42 and the cam follower 46 in FIG. 12A.

When the user releases the button 24*b*, the actuating element spring 48 forces the button 24*b* to move linearly in the distal direction 36 from the dosing state 64 back to the ready state 50. Since the button 24*b* moves in the distal direction 36, the also the cam follower 46 moves in the distal direction 36. The movement of the cam follower 46 in the distal direction 36 causes the cam follower 46 to drive the rotator 42 to rotate further by the engagement of the cam profile 44 with the cam follower 46, as shown in FIG. 12B.

As shown in FIG. 12C, the blocking structure 30 now adopts the second blocking structure position 70 where the through hole 54 is aligned with the second protrusions 40. The blocking structure 30 thereby no longer blocks movement of the plunger 26 in the proximal direction 34 by engagement between the blocking structure 30 and the second protrusions 40. The plunger spring 28 thereby forces the plunger 26 to move in the proximal direction 34.

The plunger 26 moves in the proximal direction 34 such that one pair of second protrusions 40 moves through the through hole 54 of the blocking structure 30. The movement of the plunger 26 in the proximal direction 34 causes the plunger 26 to push the stopper 20 in the proximal direction 34 to expel a first dose of medicament into the injection site. As shown in FIGS. 12A and 12C, the blocking structure 30 stops the plunger 26 when the next pair of first protrusions 38 comes in contact with the radially extending ledges of the blocking structure 30. The mechanism 12B of this example is thus configured to generate a movement of the plunger 26 in the proximal direction 34 when the button 24*b* moves from the dosing state 64 to the ready state 50.

The transmission 32 is thus arranged to transmit a transition of the button 24*b* from the ready state 50 in FIGS. 10A-10C, to the dosing state 64 in FIGS. 11A-11C, and back to the ready state 50 in FIGS. 12A-12C, to a rotation of the blocking structure 30 from the first blocking structure position 68 to the second blocking structure position 70. The next time the button 24b is moved from the ready state 50, to the dosing state 64, and back to the ready state 50, the blocking structure 30 rotates from the second blocking structure position 70 to the first blocking structure position 68. In the same way as described above, the user can perform a plurality of further deliveries of medicament or "shots" by means of the medicament delivery device 10b.

It should be noted that, alternatively, the rotator can be axially movable relative to the housing. In this case, the cam follower 46 is spaced apart from the cam profile 44 before a needle cover is moved towards the distal direction. The needle cover may lift the rotator towards the distal direction and position the cam profile 44 to the cam follower 46. The cam follower 46 will only be positioned on the distal end position of the cam profile 44 when the needle cover is pressed, so that an unintentional medicament delivery (injection in this example) by accidentally pressing the button can be prevented.

Figure 13:
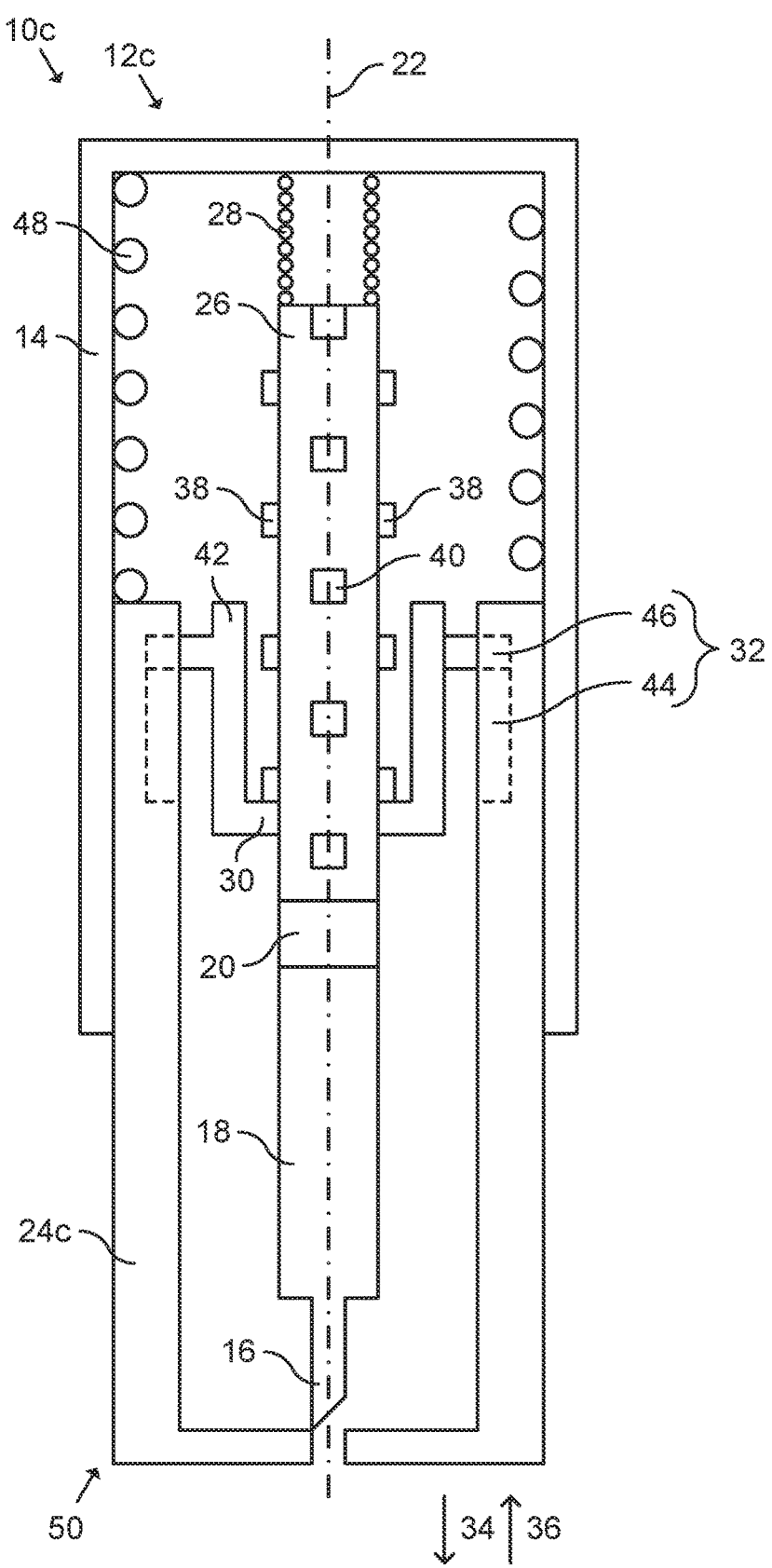
FIG. 13 schematically represents a cross-sectional side view of a further example of a medicament delivery device comprising a further example of a mechanism.

FIG. 13 schematically represents a cross-sectional side view of a further example of a medicament delivery device 10c comprising a further example of a mechanism 12c. Mainly differences with respect to FIGS. 1A-9C will be described. The medicament delivery device 10c comprises a mechanism 12c having a needle cover 24c. The needle cover 24c is a further example of an actuating element according to the present disclosure. The mechanism 12c differs from the mechanism 12a in that the cam follower 46 is provided on the rotator 42 and the cam profile 44 is provided in the needle cover 24c. When the needle cover 24c moves along the longitudinal axis 22 between the ready state 50 and the dosing state 64, the engagement between the cam follower 46 and the cam profile 44 causes the rotator 42 to rotate about the longitudinal axis 22.

Figure 14:
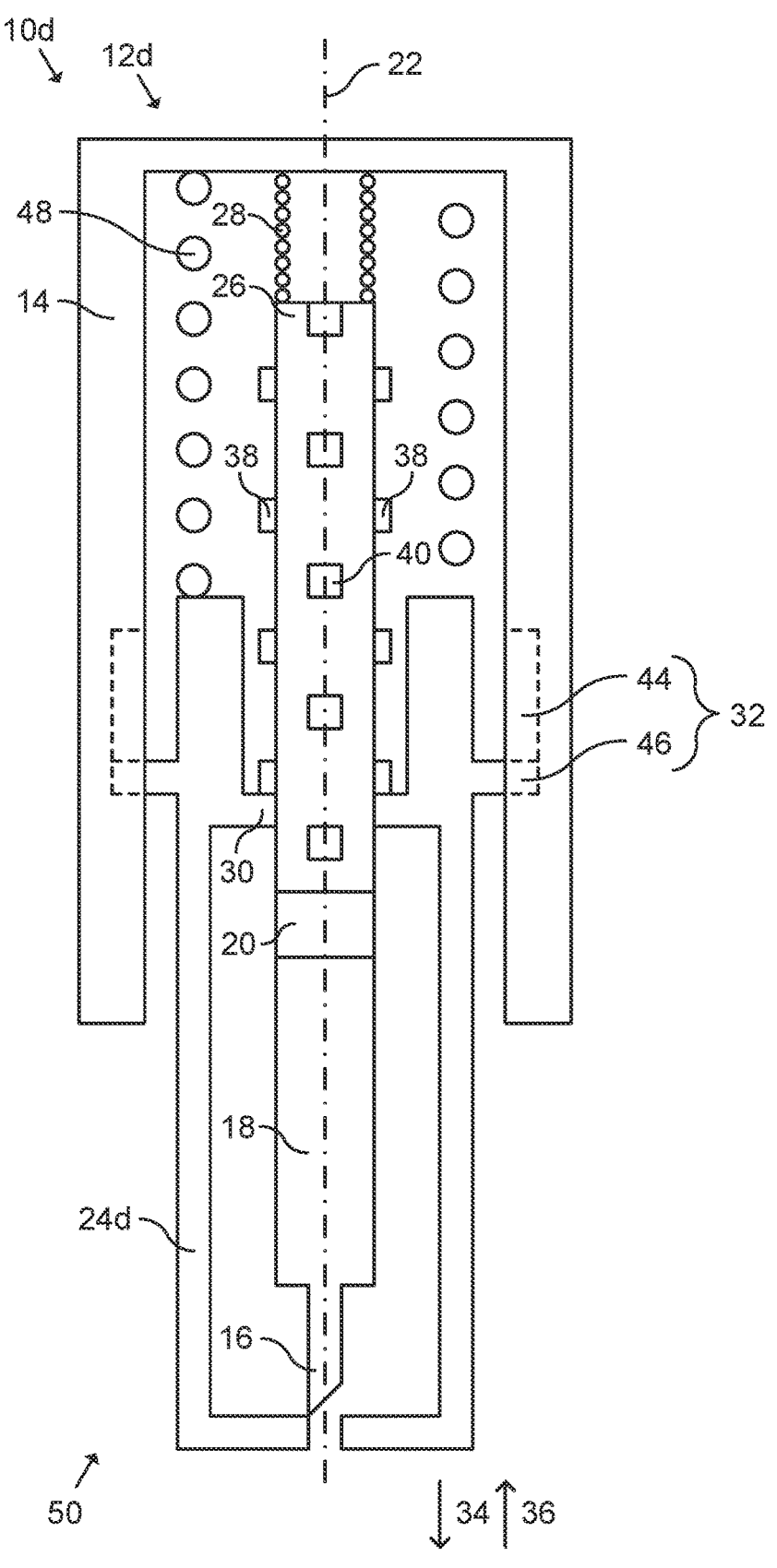
FIG. 14 schematically represents a cross-sectional side view of a further example of a medicament delivery device comprising a further example of a mechanism.

FIG. 14 schematically represents a cross-sectional side view of a further example of a medicament delivery device 10d comprising a further example of a mechanism 12d. Mainly differences with respect to FIGS. 1A-9C will be described. The medicament delivery device 10d comprises a mechanism 12d having a needle cover 24d. The needle cover 24d is a further example of an actuating element according to the present disclosure. The mechanism 12d differs from the mechanism 12a in that the cam follower 46 protrudes radially outwards from the needle cover 24d with respect to the longitudinal axis 22. The cam profile 44 is provided in the housing 14. The needle cover 24d comprises the blocking structure 30.

When the needle cover 24d moves along the longitudinal axis 22 between the ready state 50 and the dosing state 64, the engagement between the cam follower 46 and the cam profile 44 causes the needle cover 24d to rotate about the longitudinal axis 22. The rotation of the needle cover 24d causes the blocking structure 30 to move between the first blocking structure position 68 and the second blocking structure position 70. The needle cover 24d thereby functions as a rotator but the mechanism 12d does not comprise any dedicated rotator. Instead, the needle cover 24d controls the plunger 26.

Figure 15:
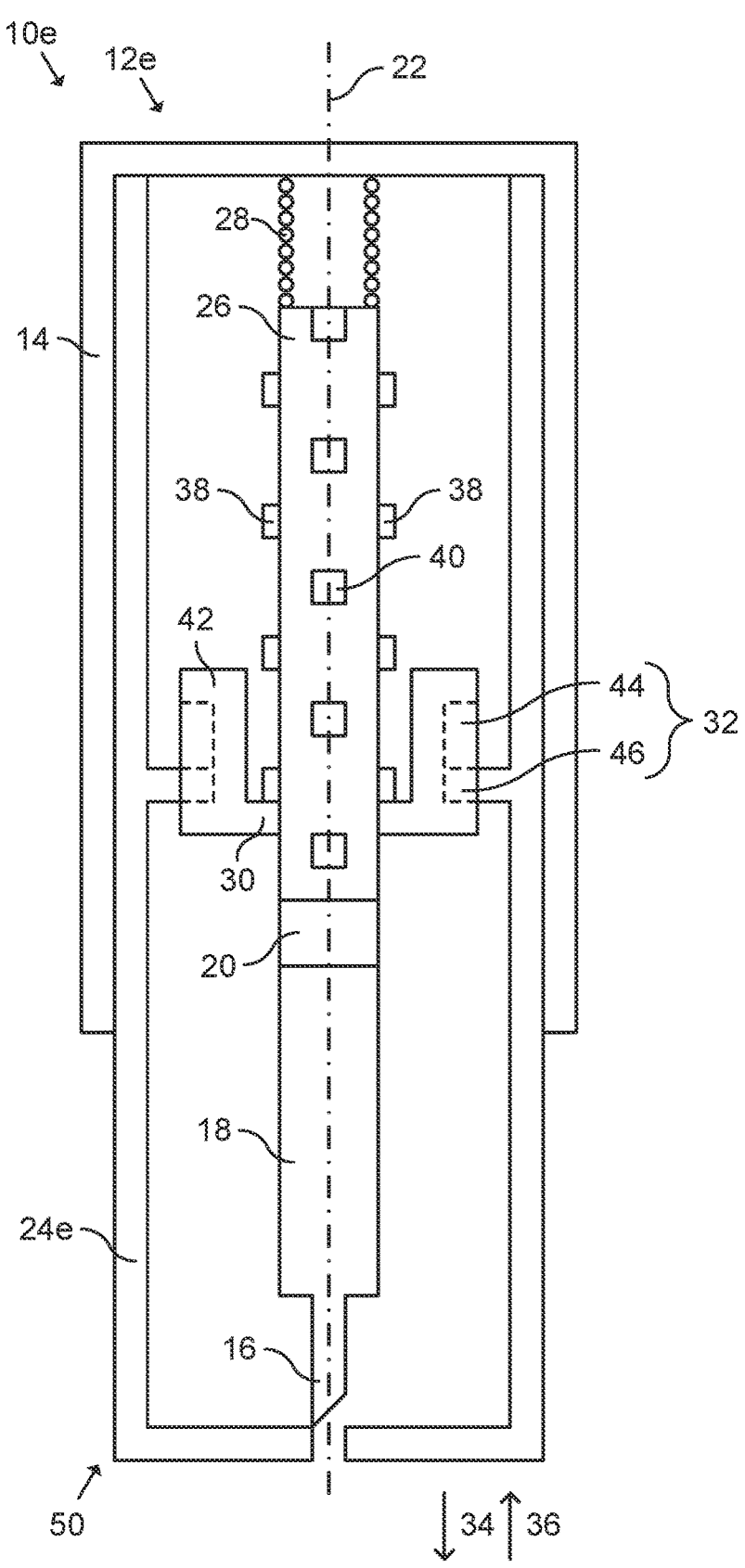
FIG. 15 schematically represents a cross-sectional side view of a further example of a medicament delivery device comprising a further example of a mechanism with an actuating element in a ready state.

FIG. 15 schematically represents a cross-sectional side view of a further example of a medicament delivery device 10e comprising a further example of a mechanism 12e. Mainly differences with respect to FIGS. 1A-9C will be described. The medicament delivery device 10e comprises a mechanism 12e having a needle cover 24e. The needle cover 24e is a further example of an actuating element according to the present disclosure. The needle cover 24e is flexible.

The mechanism 12e does not comprise any actuating element spring. A distal end of the needle cover 24e is fixed to the housing 14. In FIG. 15, the needle cover 24e is in the ready state 50. In the ready state 50, the needle cover 24e is in a resting state.

Figure 16:
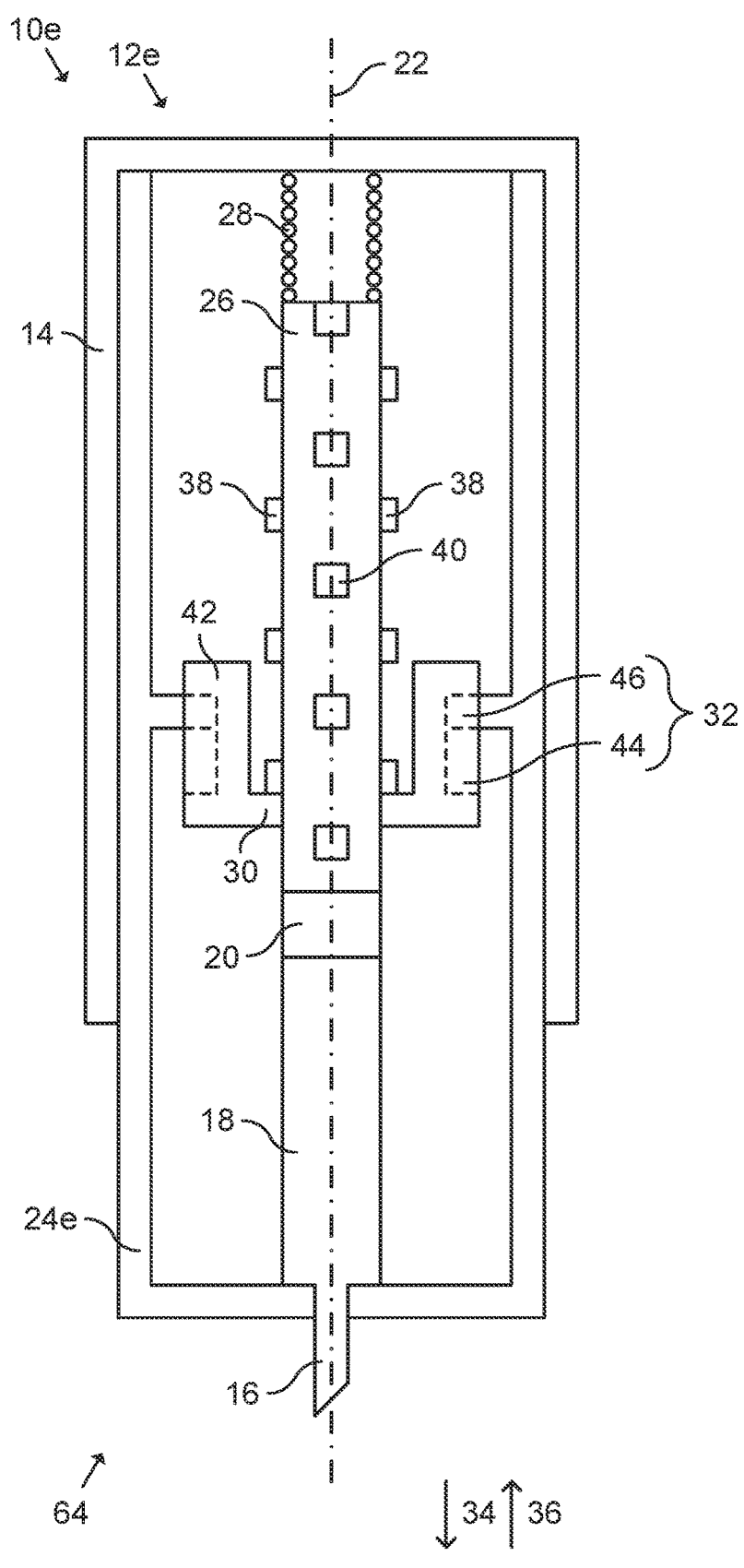
FIG. 16 schematically represents the medicament delivery device in FIG. 15 when the actuating element adopts a dosing state.

FIG. 16 schematically represents the medicament delivery device 10e in FIG. 15 when the needle cover 24e adopts the dosing state 64. As shown in FIG. 16, the needle cover 24e transitions from the ready state 50 to the dosing state 64 by deformation of the needle cover 24e from the resting state. In the dosing state 64, the needle cover 24e has been compressed in the distal direction 36 by pushing the medicament delivery device 10e against an injection site (not shown). This compression of the needle cover 24e causes the cam follower 46 to move in the distal direction 36 to drive the rotator 42 to rotate about the longitudinal axis 22 by the engagement of the cam profile 44 with the cam follower 46. Since a movement of a proximal end of the needle cover 24e in the distal direction 36 is larger than a movement of the cam follower 46 in the distal direction 36 during the transition from the ready state 50 to the dosing state 64, a size of the cam profile 44 along the longitudinal axis 22 can be reduced in comparison with FIGS. 1A-9C.

When the medicament delivery device 10e is removed from the injection site, the needle cover 24e expands and returns to the ready state 50. This expansion of the needle cover 24e causes the cam follower 46 to move in the proximal direction 34 to drive the rotator 42 to rotate further about the longitudinal axis 22 by the engagement of the cam profile 44 with the cam follower 46. The actuating element spring can thereby be eliminated by making use of the flexibility of the needle cover 24e itself.

While the present disclosure has been described with reference to exemplary embodiments, it will be appreciated that the present disclosure is not limited to what has been described above. For example, it will be appreciated that the dimensions of the parts may be varied as needed. Accordingly, it is intended that the present disclosure may be limited only by the scope of the claims appended hereto.

The invention claimed is:

1. A mechanism for a medicament delivery device, the mechanism comprising:
    an actuating element configured to adopt a ready state and a dosing state;
    a longitudinal axis;
    a plunger comprising at least one first blocking feature and at least one second blocking feature, where the at least one first blocking feature and the at least one second blocking feature are axially and circumferentially offset from each other with respect to the longitudinal axis;
    a plunger force device arranged to force the plunger in a proximal direction along the longitudinal axis;
    a blocking structure rotatable about the longitudinal axis from a first blocking structure position, in which one of the at least one first blocking feature is allowed to pass by the blocking structure and one of the at least one second blocking feature is prevented from passing by the blocking structure, and a second blocking structure position, in which one of the at least one second blocking feature is allowed to pass by the blocking structure; and
    a transmission configured to transmit a transition of the actuating element between the ready state and the dosing state to a rotation of the blocking structure from the first blocking structure position to the second blocking structure position.

2. The mechanism according to claim 1, wherein the blocking structure comprises a through hole; wherein when in the first blocking structure position, the through hole is aligned with the at least one first blocking feature, and the through hole is misaligned with the at least one second blocking feature; and wherein when in the second blocking structure position, the through hole is aligned with the at least one second blocking feature.

3. The mechanism according to claim 1, wherein the transmission is configured to transmit a transition of the actuating element from the dosing state to the ready state and back to the dosing state, or a transition of the actuating element from the ready state to the dosing state and back to the ready state, to a rotation of the blocking structure from the first blocking structure position to the second blocking structure position.

4. The mechanism according to claim 1, wherein each of the at least one first blocking feature and the at least one second blocking feature comprises a protrusion protruding radially outwards with respect to the outer surface of the plunger.

5. The mechanism according to claim 1, wherein the at least one first blocking feature is a plurality of first blocking features and the at least one second blocking feature is a plurality of second blocking features, and wherein the first blocking features and the second blocking features are alternatingly arranged along the longitudinal axis.

6. The mechanism according to claim 5, wherein the first blocking features and the second blocking features are evenly distributed along the longitudinal axis.

7. The mechanism according to claim 1, wherein the transmission comprises a cam profile and a cam follower arranged to follow the cam profile.

8. The mechanism according to claim 7, wherein the cam profile comprises a plurality of cam profile sections, and wherein each relative movement between the cam follower and the cam profile through one of the cam profile sections is transmitted to a rotation of the blocking structure between the first blocking structure position and the second blocking structure position.

9. The mechanism according to claim 7, wherein the mechanism comprises a rotator, wherein the rotator comprises the blocking structure.

10. The mechanism according to claim 7, wherein the cam profile is provided on the rotator.

11. The mechanism according to claim 7, wherein the cam follower is provided on the actuating element.

12. The mechanism according to claim 7, wherein the cam profile is provided on the actuating element.

13. The mechanism according to claim 1, wherein the actuating element (24a-24d) is movable along the longitudinal axis between the ready state and the dosing state.

14. The mechanism according to claim 1, further comprising an actuating element force device arranged to force the actuating element from the dosing state to the ready state.

15. A medicament delivery device comprising a mechanism according to claim 1, and a medicament container.

16. A mechanism for a medicament delivery device, the mechanism comprising:

an actuating element having a ready state and a dosing state;

a longitudinal axis;

a plunger comprising two first blocking protrusions and two second blocking protrusions, where the first blocking protrusions and the second blocking protrusions extend radially outward from a surface of the plunger and are axially and circumferentially offset from each other with respect to the longitudinal axis;

a spring partially positioned inside the plunger;

a blocking structure rotatable about the longitudinal axis from a first blocking structure position to a second blocking structure position; and a transmission that transmits a transition of the actuating element between the ready state and the dosing state to a rotation of the blocking structure from the first blocking structure position to the second blocking structure position.

17. The mechanism of claim 16, wherein when in the first blocking structure position one of the first blocking feature is allowed to pass by the blocking structure and one of the second blocking feature is prevented from passing by the blocking structure.

18. The mechanism of claim 16, wherein when in the second blocking structure position one of the second blocking feature is allowed to pass by the blocking structure.

19. The mechanism of claim 18 further comprises a rotator that comprises the blocking structure and a cam profile, where a cam follower is located on the actuating element.

20. A medicament delivery device comprising a mechanism of claim 19 and medicament container.

\* \* \* \* \*